United States Patent [19]

Herzog et al.

[11] 4,206,130
[45] Jun. 3, 1980

[54] PROCESS FOR THE PREPARATION OF 1,5-DICHLOROANTHRAQUINONE

[75] Inventors: Helmut Herzog; Walter Hohmann, both of Leverkusen; Helmut Seidler, Bonn, all of Fed. Rep. of Germany

[73] Assignee: Bayer Aktiengesellschaft, Leverkusen, Fed. Rep. of Germany

[21] Appl. No.: 898,262

[22] Filed: Apr. 20, 1978

[30] Foreign Application Priority Data

May 10, 1977 [DE] Fed. Rep. of Germany ....... 2720965
Sep. 3, 1977 [DE] Fed. Rep. of Germany ....... 2739840

[51] Int. Cl.² .............................................. C07C 49/68
[52] U.S. Cl. ..................................... 260/384; 260/684
[58] Field of Search ................................. 260/384, 684

[56] References Cited

U.S. PATENT DOCUMENTS

| 1,969,044 | 8/1934 | Shaw et al. | 260/384 |
| 4,006,171 | 2/1977 | Majer et al. | 260/384 |

FOREIGN PATENT DOCUMENTS 178390  2/1966  U.S.S.R. .................................. 260/384

Primary Examiner—Winston A. Douglas
Assistant Examiner—Raymond K. Covington
Attorney, Agent, or Firm—Sprung, Felfe, Horn, Lynch & Kramer

[57] ABSTRACT

A process has been invented for the preparation of 1,5-dichloroanthraquinone which comprises reacting 1,5-dichloroanthraquinone with chlorine in the presence of at least 50% by weight of liquid phthalic anhydride, relative to the weight of 1,5-dinitroanthraquinone employed. The 1,5-dichloroanthraquinone is known to be a valuable starting material for the preparation of various dyestuffs.

8 Claims, No Drawings

PROCESS FOR THE PREPARATION OF 1,5-DICHLOROANTHRAQUINONE

The present invention relates to a new process for the preparation of 1,5-dichloroanthraquinone by the action of chlorine on 1,5-dinitroanthraquinone.

A process for the preparation of α- and β-chloroanthraquinones in which α- and β-nitroanthraquinones are reacted with elementary chlorine, optionally in solvents, such as trichlorobenzene, at temperatures of, for example 150° to 185° C., is described in German Patent Nos. 252,578 and 254,450. However, the good yields of chloroanthraquinones supposedly obtained by this process could not be reproduced (compare F. H. Day, J. Chem. Soc. 1939, page 817).

A further process for the preparation of chloroanthraquinones consists in chlorinating nitroanthraquinones in bulk or as a mixture with sodium chloride at temperatures of 270° C. to 290° C. (USSR Inventor's Certificate 178,390). However, in attempts to repeat the process, the yields of 90% indicated in this publication, could not be achieved by far. In addition, this reaction has all the disadvantages of a solid/gas reaction, for example the temperature control is difficult and long reaction times are required.

A process has now been found for the preparation of 1,5-dichloroanthraquinone from 1,5-dinitroanthraquinone by reaction with elementary chlorine at elevated temperature, which is characterized in that the reaction is carried out in the presence of at least 50% by weight of liquid phthalic anhydride, relative to the weight of 1,5-dinitroanthraquinone employed, and the phthalic anhydride is separated off after the reaction.

Dinitroanthraquinone mixtures which predominantly contain 1,5-dinitroanthraquinone, or pure or industrial 1,5-dinitroanthraquinone can be employed in the process according to the invention. If industrial 1,5-dinitroanthraquinone or dinitroanthraquinone mixtures which predominantly contain 1,5-dinitroanthraquinone are employed, the feed material can contain, in addition to 1,5-dinitroanthraquinone, other nitroanthraquinones, for example 1- and/or 2-mononitroanthraquinone and/or 1,6-, 1,7-, 1,8-, 2,6- and/or 2,7dinitroanthraquinone. Furthermore, the feed material can contain relatively small amounts of anthraquinone and/or by-products formed during the nitration of anthraquinone. Pure or industrial 1,5-dinitroanthraquinone is preferably employed in the process according to the invention.

1,5-Dichloroanthraquinone is obtained in relatively high yield from the 1,5-dinitroanthraquinone employed. If the feed material also contains other nitroanthraquinones, in general these are also converted into the corresponding chloroanthraquinones.

Elementary chlorine is employed in the gaseous form in the process according to the invention. It is appropriate to avoid relatively large excesses of chlorine, since otherwise there is the danger of more highly chlorinated by-products being formed, especially at relatively high reaction temperatures. In general, gaseous elementary chlorine is passed in, until no further nitrous gases escape from the reaction mixture. It is also possible to follow the progress of the reaction analytically, for example by thin layer chromatography or gas chromatography, and to stop feeding in chlorine when 1,5-dinitroanthraquinone can no longer be detected.

Suitable temperatures for carrying out the process according to the invention are, for example, temperatures in the range from 170° C. to 260° C. Temperatures in the range between 200° and 250° are preferably used. The process according to the invention can be carried out under normal pressure or slightly elevated pressure.

An essential characteristic of the process according to the invention is that it can be carried out in the presence of liquid phthalic anhydride. In general, it is sufficient to employ at least 50% by weight of phthalic anhydride relative to the weight of 1,5-dinitroanthraquinone, in the process according to the invention. It is possible, for example, to use phthalic anhydride in amounts between 0.5 and 20 mols per mol of nitroanthraquinone employed. Between 2 and 6 mols of phthalic anhydride per mol of 1,5-dinitroanthraquinone are preferably employed. The chlorine utilisation is particularly good if the 1,5-dinitroanthraquinone, together with phthalic anhydride, give a thinly liquid melt which can be easily stirred. The amounts of phthalic anhydride relative to a particular amount of 1,5-dinitroanthraquinone or a particular 1,5-dinitroanthraquinone mixture which form such thinly liquid melts can optionally be determined by plotting a melt diagram.

The reaction mixture, which essentially contains phthalic anhydride and 1,5-dichloroanthraquinone, can be worked up in a simple manner. Firstly, it is advantageous to blow out the chlorine still present in the melt, using a stream of inert gas, for example nitrogen. It is then possible, for example, to distil off the phthalic anhydride, preferably in vacuo, or to dissolve out the phthalic anhydride by treatment with hot water. The chloroanthraquinone mixture which remains, containing 1,5-dichloroanthraquinone or predominantly 1,5-dichloroanthraquinone, contains virtually no impurities. If, in addition to 1,5-dinitroanthraquinone, other nitroanthraquinones are also employed in the process according to the invention, and as a result mixtures which also contain, in addition to a predominant amount of 1,5-dichloroanthraquinone, other chloroanthraquinones are obtained, it is possible to separate these chloroanthraquinone mixtures into individual fractions or pure isomers, for example by rectification. For this, for example, the procedure followed can be according to DT-OS (German Published Specification) No. 2,458,022. If such a working-up of a chloroanthraquinone mixture is carried out, the phthalic anhydride is appropriately separated off from the melt present after the reaction, in a first rectification stage via the head.

If the phthalic anhydride is separated off by distillation, it can be advantageous to remove, for example, only 80 to 95% of the phthalic anhydride employed and then to treat the mixture present with a suitable solvent, under the influence of heat. After cooling and filtering the mixture, purer 1,5-dichloroanthraquinone is obtained as the residue than is obtained when the phthalic anhydride is completely separated off by distillation. Examples of suitable solvents are nitrobenzene, chlorobenzenes and dimethylformamide.

The process according to the invention can be carried out in a continuous or discontinuous procedure.

In the case of the discontinuous procedure, 1,5-dinitroanthraquinone and phthalic anhydride can be mixed in the proportions indicated or, after plotting the melt diagram, in those proportions which give a thinly liquid melt at the reaction temperature. The temperature can then be adjusted to within the range from 170° C. to 260° C., preferably between 200° and 250° C., by applying heat externally. The introduction of elementary chlorine can then be started. The chlorine is appropriately introduced in such amounts per unit time that, as far as possible, no excess chlorine escapes from the reaction vessel. After the reaction has ended, the reaction mixture can be worked up as described above, by feeding it in the liquid form to a distillation apparatus. However, it can also be advantageous to first pour the melt onto a metal sheet after the reaction has ended, to leave it solidify there, subsequently to comminute it and then to separate off the phthalic anhydride.

In the case of the continuous procedure, the reaction can be carried out by continuously feeding phthalic anhydride and 1,5-dinitroanthraquinone, separately or as a mixture, into a multi-stage bubble column and gassing the mixture with chlorine, preferably in a counter-current process. The completely reacted reaction melt is withdrawn at the foot of the column via a syphon at the same rate at which the feed materials are fed in at the head of the bubble column.

Before separating off the phthalic anhydride, the reaction melt is preferably passed over a flaking roller, where cooling and comminution take place. The phthalic anhydride can then be separated off from the 1,5-dichloroanthraquinone by one of the procedures described above.

The process according to the invention makes it possible to prepare 1,5-dichloroanthraquinone from 1,5-dinitroanthraquinone, or mixtures which predominantly contain 1,5-dinitroanthraquinone, in good yields, products which contain virtually no by-products being obtained. The phthalic anhydride employed in the process according to the invention can be re-used after being separated off. If the separation of the phthalic anhydride is effected by treatment with hot water, the phthalic anhydride is converted into phthalic acid. However, it is possible to reconvert this phthalic acid into phthalic anhydride in a manner which is in itself known and to re-use this. 1,5-Dichloroanthraquinone can be prepared from 1,5-dinitroanthraquinone and chlorine at relatively low temperatures in the process according to the invention.

The 1,5-dichloroanthraquinone obtainable by the process according to the invention is a known, valuable starting material for the preparation of vat dyestuffs (compare Ullmann, Enzyklopädie der technischen Chemie (Ullmann's Encylopedia of Industrial Chemistry), 4th edition (1973), volume 7, page 631), of acid dyestuffs for wool (by reaction with amines and subsequent sulphonation, compare U.S. Pat. No. 2,605,269 and DT-OS (German Published Specification) No. 2,050,961) and of disperse dyestuffs (by reaction with amines, compare British Patent No. 1,081,890, or by reaction with thiophenols or sulphinates, compare DT-OS (German Published Specification) No. 1,644,578).

The process according to the invention may be illustrated in more detail with the aid of the following Examples, but without being limited to these Examples.

EXAMPLES

EXAMPLE 1

(a) 900 g of phthalic anhydride are melted at 200° C. in a thermostatically controlled 1 l glass vessel with a ground glass flange, which has an internal diameter of 100 mm and a height of 205 mm and is fitted with an anchor stirrer and a gas inlet tube which is flared at the bottom. 300 g of ground 98% pure 1,5-dinitroanthraquinone are introduced into this melt in the course of a few minutes. A stream of chlorine of 11 l of chlorine per hour is then passed into this melt at 240° to 245° C. for 150 minutes. Brown reaction gases are immediately evolved, and after about 60 minutes the suspension passes into a clear melt. The course of the reaction is monitored by removing a sample from the melt, by dipping a glass rod in, and examining it by chromatography in accordance with customary methods. The reaction has ended as soon as the evolution of nitrous gases ceases and feed material can no longer be detected by thin layer chromatography. Thereafter, the melt is blown free from chlorine in the reaction vessel at 200° C. by passing nitrogen in, and is then poured onto an enamel sheet, where the melt is allowed to solidify. 1,158 g of a mixture of phthalic anhydride and 1,5-dichloroanthraquinone, which contains 21.5% of 1,5-dichloroanthraquinone (91.2% of theory) and is free from 1,5-dinitroanthraquinone, are obtained in this manner. The chlorine content of the reaction product is 6.5%.

(b) 100 g of powdered melt product from (a) are heated in 1 l of water at 90° to 100° C. for about 45 minutes, whilst stirring well. The mixture is then filtered hot at the boil and the residue on the filter is rinsed with hot water and dried at 100° C. 22.1 g of 94% pure 1,5-dichloroanthraquinone, which has a chlorine content of 25%, are thus obtained; the melting point is 246° to 249° C.

(c) 810 g of phthalic anhydride (90% of the material employed) are removed from the crude product from a) by vacuum distillation. 300 ml of nitrobenzene are then added to the cooled, powdered distillation residue and the mixture is heated to 200° to 210° C., whilst stirring, whereupon a solution forms, and is kept at this temperature for 15 minutes. The mixture is subsequently stirred until the temperature reaches 20°–25° C. and is filtered at this temperature and the residue is first washed with 300 ml of nitrobenzene and then with methanol until free from nitrobenzene and dried at 100° C. 250 g (86.8% of theory) of 1,5-dichloroanthraquinone are thus obtained in a purity of 96%.

If the nitrobenzene is replaced by trichlorobenzene, o-dichlorobenzene, chlorobenzene or dimethylformamide, the mixture is heated up to the boiling point of the solvent, whilst stirring, whereupon a solution forms, and is kept at the reflux temperature for about 15 minutes and the procedure is otherwise similar to that indicated under (c), a 92 to 94% pure 1,5-dichloroanthraquinone is obtained in good yield.

EXAMPLE 2

The procedure followed is as indicated under Example 1 (a), but the reaction temperature, the rate of the stream of chlorine, the reaction time and the proportion of phthalic anhydride to 1,5-dinitroanthraquinone, is changed. The amounts employed, reaction conditions and results can be seen from Table 1.

Table 1

| Example | Amounts employed g of PA | g of 1,5-DNA | Temperature (°C.) | Stream of chlorine (l/hour) | Reaction time (minutes) | Result (g of PA + 1,5-DCA) | Content of 1,5-DCA (%) | Yield of 1,5-DCA (% of theory) | Chlorine content (%) |
|---|---|---|---|---|---|---|---|---|---|
| 2 a | 450 | 150 | 220–225 | 11 | 120 | 573 | 21.7 | 91.2 | 6.6 |
| 2 b | 800 | 400 | 238–242 | 11 | 210 | 1,148 | 28.8 | 90.6 | 8.5 |
| 2 c | 700 | 500 | 238–242 | 11 | 260 | 1,136 | 35.9 | 89.5 | 10.5 |
| 2 d | 900 | 300 | 240–245 | 16 | 150 | 1,158.2 | 19.6 | 83.2 | 6.6 |
| 2 e | 900 | 300 | 249–253 | 11 | 150 | 1,155 | 20.2 | 85.5 | 6.5 |
| 2 f | 1,000 | 200[1] | 238–242 | 9 | 120 | 1,169[2] | 12.2 | 90.5 | 3.6 |

PA = phthalic anhydride
DNA = dinitroanthraquinone
PCA = dichloroanthraquinone
[1]Analysis: 85% of 1,5-DNA; 15% of 1,8-DNA;
[2]Analysis: 12.2% of 1,5-DCA, 2.14% of 1,8-DCA; remainder PA

EXAMPLE 3

A mixture of 100 g of 98% pure 1,5-dinitroanthraquinone and 400 g of phthalic anhydride is melted at 200° C. in a pan and the melt is introduced into a bubble column (height 300 mm, diameter 40 mm D-2 bottom frit), through the bottom frit of which a light stream of nitrogen is passed. After shutting off the nitrogen, a stream of chlorine of 4 l of chlorine per hour is then passed through the melt at 240° C. for 150 minutes. Brown reaction gases are immediately evolved. The course of the reaction is monitored by removing a sample from the melt, by dipping a glass rod in, and examining it by thin layer chromatography in accordance with customary methods.

After the reaction has ended, that is to say after 1,5-dinitroanthraquinone is no longer found by thin layer chromatography in a sample removed, the melt is flushed with nitrogen (11 l per hour) for 15 minutes in order to remove the reaction gases, poured out of the bubble column onto a metal sheet and, after cooling, is powdered. 483 g of a yellow solid with a 1,5-dichloroanthraquinone content of 16.9% are obtained, which corresponds to a yield of 1,5-dichloroanthraquinone of 89.8% of theory. The chlorine content of the reaction product is 5%. No unreacted 1,5-dinitroanthraquinone can be detected.

EXAMPLE 4

A multi-stage bubble column which consists of 10 courses (length 2,000 mm, diameter 100 mm) and is fitted with perforated trays and overflow tubes, is charged continuously at the head with a mixture of 98% pure 1,5-dinitroanthraquinone and phthalic anhydride (8.55 kg of phthalic anhydride and 1.45 kg of 1,5-dinitroanthraquinone/hour), which is melted by heating to 200° C. Gaseous chlorine (110 l/hour) is passed into this melt in countercurrent, the temperature being kept at 240° to 245° C. Whilst flowing through the column, the dinitroanthraquinone is completely converted into 1,5-dichloroanthraquinone, which leaves the column, together with phthalic anhydride, via a syphon. The reaction gases are drawn off via the head. The reaction product contains 13.3% of 1,5-dichloroanthraquinone; the chlorine content is about 4%.

What is claimed is:

1. Process for the preparation of 1,5-dichloroanthraquinone which comprises reacting 1,5-dinitroanthraquinone with elementary chlorine at elevated temperature, in the presence of at least 50% by weight of liquid phthalic anhydride, relative to the weight of 1,5-dinitroanthraquinone employed, and separating off the phthalic anhydride after the reaction is completed.

2. Process according to claim 1, characterized in that between 0.5 and 20 mols of phthalic anhydride are employed per mol of 1,5-dinitroanthraquinone.

3. Process according to claim 1, characterized in that between 2 and 6 mols of phthalic anhydride are employed per mol of 1,5-dinitroanthraquinone.

4. Process according to claim 1, characterized in that the reaction is carried out at temperatures from 170° C. to 260° C.

5. Process according to claim 1, characterized in that the reaction is carried out at temperatures from 200° and 250° C.

6. Process according to claim 1, characterized in that the reaction is carried out continuously in a bubble column.

7. Process according to claim 1, characterized in that after the reaction phthalic anhydride is separated off by vacuum distillation.

8. Process according to claim 1, characterized in that after the reaction phthalic anhydride is separated off by treatment with hot water.

* * * * *